United States Patent [19]

Johnson

[11] 4,348,910
[45] Sep. 14, 1982

[54] SPONGE IRON PRODUCTS SAMPLING DEVICE

[75] Inventor: Gorden F. Johnson, Pittsburgh, Pa.

[73] Assignee: Pullman Incorporated, Chicago, Ill.

[21] Appl. No.: 243,291

[22] Filed: Mar. 13, 1981

Related U.S. Application Data

[63] Continuation of Ser. No. 88,887, Oct. 29, 1979, abandoned.

[51] Int. Cl.³ ............................................... G01N 1/20
[52] U.S. Cl. ................................ 73/863.51; 73/863.58
[58] Field of Search ........... 73/863.41, 863.43, 863.51, 73/863.58

[56] References Cited

U.S. PATENT DOCUMENTS

| | | | |
|---|---|---|---|
| 2,076,861 | 4/1937 | Parsons | 73/863.41 |
| 2,208,167 | 7/1940 | Shular | 73/863.41 |
| 3,478,597 | 11/1959 | Merigold | 73/863.58 |
| 3,955,680 | 5/1976 | Botula | 209/676 |
| 3,978,986 | 9/1976 | Schmidt | 209/676 |
| 4,080,831 | 3/1978 | Roberts | 73/863.61 |

Primary Examiner—S. Clement Swisher
Attorney, Agent, or Firm—Richard J. Myers

[57] ABSTRACT

A product sampling apparatus for taking sponge iron sample pellets as they are moved by a conveyor from a direct ore reduction process includes upper and lower chambers, one of which is in communication with a sampling station, and the other which returns a portion of the sample to the conveyor. The apparatus includes a collector end desponed within the conveyer and includes a surface having deflectors baffles and openings which direct a typical representative portion of the product mix being sampled to the two chambers, one returning the portion to the conveyor and the other to the sampling station.

8 Claims, 3 Drawing Figures

SPONGE IRON PRODUCTS SAMPLING DEVICE

This is a continuation of Ser. No. 088,887, filed Oct. 29, 1979 now abandoned.

BACKGROUND OF THE INVENTION

1. Field of the Invention

The present invention relates to a product sampling device particularly useful in the steel making industry wherein sponge iron pellets are conveyed from a gaseous reduction vessel to another location and where it is desired to periodically sample the pellets which are produced.

2. Description of the Prior Art

A pertinent patent is U.S. Pat. No. 2,076,861 Apr. 13, 1937, which shows a sample splitter having a certain likeness to the present invention. However, the sample splitter shown in this patent is primarily concerned with securing a sample portion of material such as coals, seeds, grains, etc. by merely pouring the entire amount through the sampling apparatus. In the sampler thus shown the primary intention is to separate a certain amount of the sample from the rest of the bulk, wherein the present invention only a portion of the material, which is in this case sponge iron, is conducted through the sampling apparatus to a sampling station. This portion is representative or typical of the product mix and the remainder is returned thru a chute to the conveyor. Thus the prior art which is pertinent does not disclose the specific arrangement of the present product sampling apparatus which is highly effective in providing a typical portion of a product mix.

SUMMARY OF THE INVENTION

In the present invention a sampling device is combined with a conveyor which transports sponge iron pellets from a gaseous reduction vessel. The conveyor is of a tubular type and has included therein a sampler provided at its upper end with a funnel shaped collector or hopper end randomly capturing sponge iron pellets and delivering them to the sampler which includes a two chambered housing with the upper chamber receiving product from the conveyor which is discharged from the upper chamber either downwardly into a lower chamber or outwardly through a pipe connection from which subsequently the sample is removed for testing as desired. The sponge iron pellets which are discharged into the lower chamber are subsequently returned to the conveyor by means of a discharge channel connected to an opening within the conveyor.

An intermediate wall of the sampler apparatus is provided with a plurality of openings. The first openings are disposed in a complete row extending transversly across the receiving end of the housing and include vertically extending baffles to divert certain portions of sponge iron pellets downwardly into the lower chamber whereupon it is subsequently returned again to the conveyor. The row of openings also includes openings of a different size and configuration with suitable deflectors to assure that every sample being collected is typical of the total being conveyed.

The positioning of the openings, size, and deflectors in the upper chambers are much that the flow of materials over the surface and between the chambers is unique and efficiently handled providing a sample representative and typical of the total sponge iron mix.

The various shaped cut out portions in the intermediate wall, adjacent to the collector pipe, provide for the ready discharge of the larger pellets down into the second or lower chamber as desired. Thus the present sampler is distinctive in that the arrangement of the baffles and openings is a representative or typical sample of the sponge iron mix is provided.

DESCRIPTION OF THE PREFERRED EMBODIMENT

Figure 1:
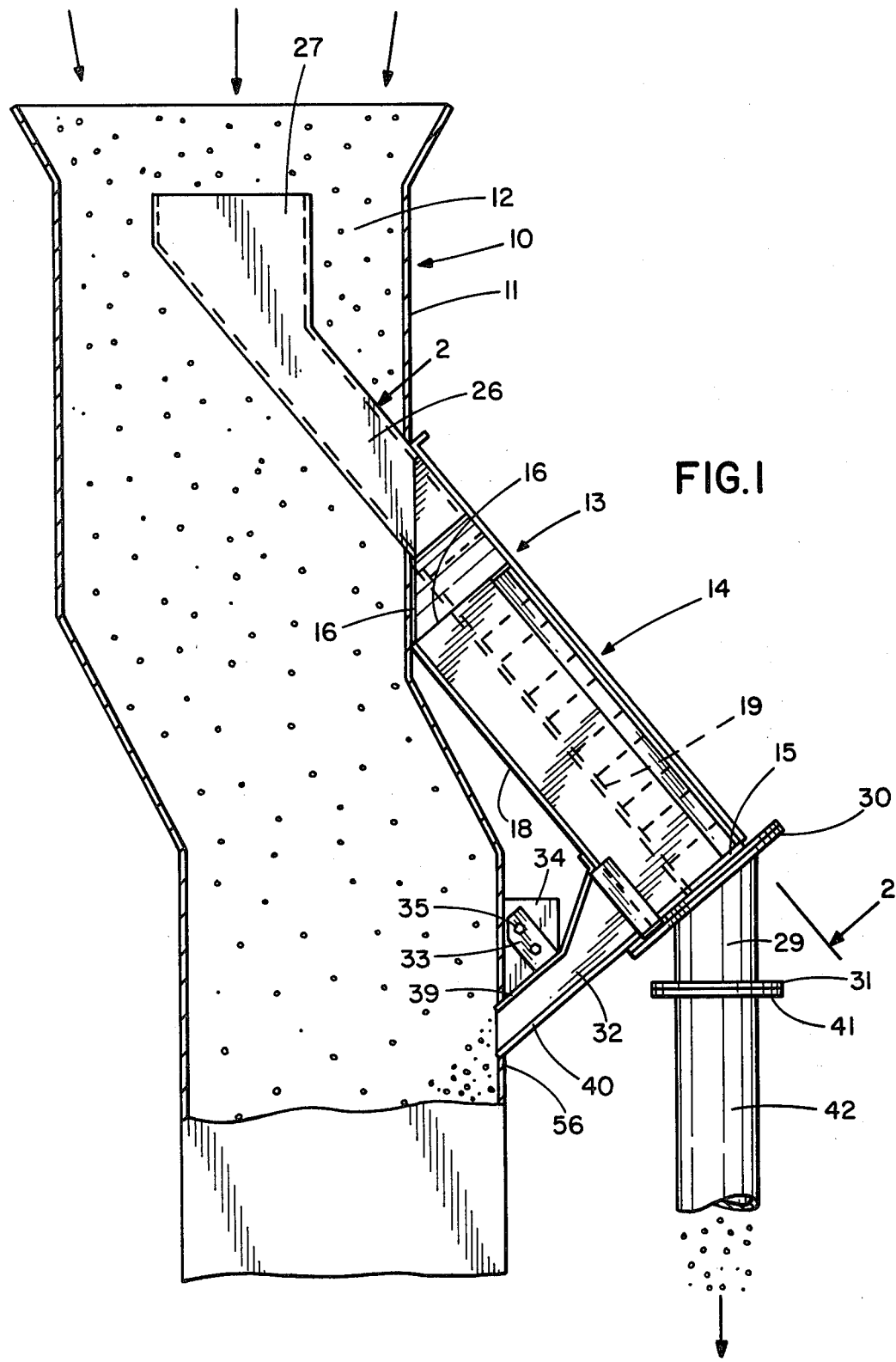
FIG. 1 is a cross-sectional view through a conveyor disclosing a sampling apparatus connected thereto.
Figure 2:
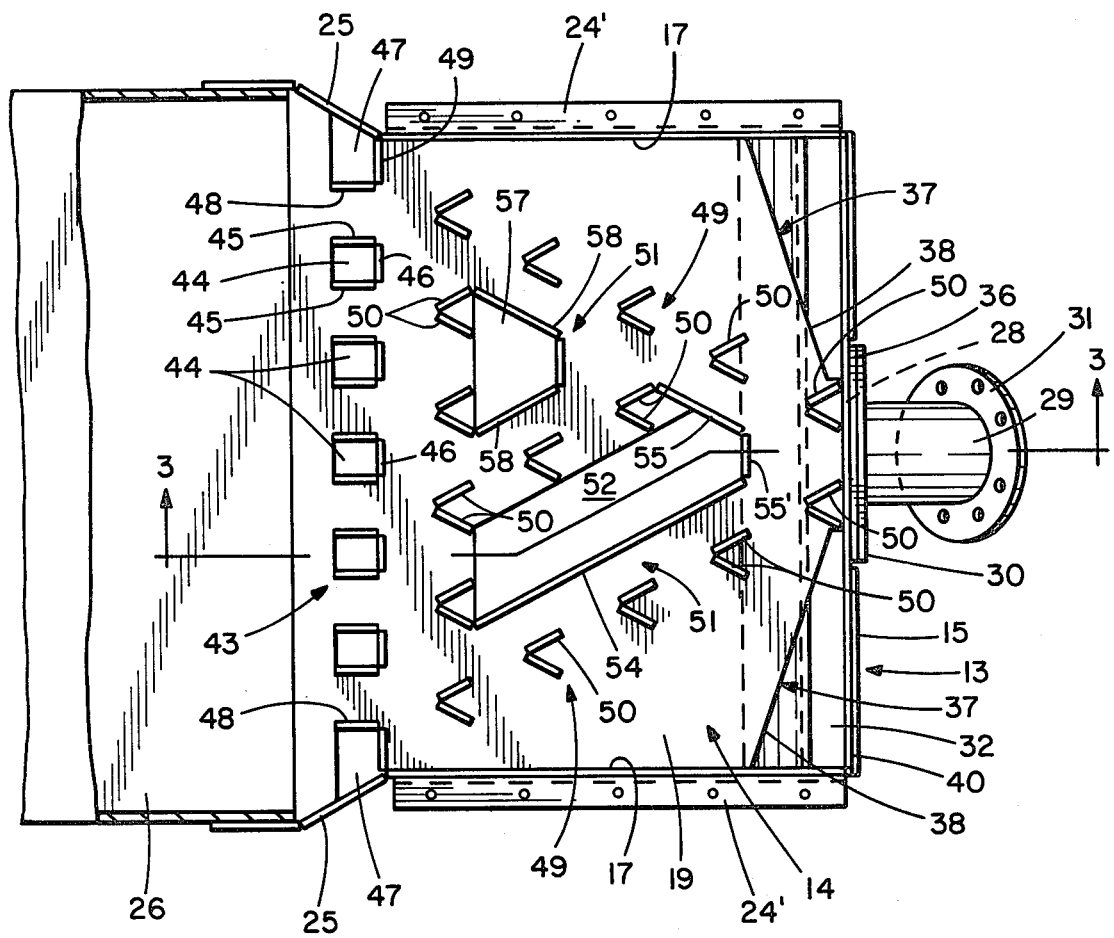
FIG. 2 is a cross-sectional view taken along the line 2—2 of FIG. 1.

FIG. 1 discloses a conveyor generally designated by the reference character 10. The conveyor is of a conduit type including a tubular member 11 through which sponge iron pellets 12 are delivered from a suitable conveyor arrangement adapted to convey the sponge iron produced by a direct gaseous reduction process from a reduction vessel. A vessel of the type which will produce sponge iron pellets is disclosed in the Celada U.S. Pat. No. 3,467,368 and a gaseous reduction process is disclosed in Celada U.S. Pat. No. 2,900,247. The sponge iron pellets are conveyed by the conveyor 10 onto and beyond a product sampler apparatus generally designated at 13. The product sampler apparatus 13 comprises a housing 14 having opposed end walls 15 and 16 suitably connected to side wall 17. The housing 14 includes a horizontal bottom wall 18 and an intermediate wall 19 also connected to walls 15 and 17. The housing 14 thus is divided into an upper chamber 20 and a lower chamber 21. The upper chamber 20 is covered by a top cover 22 which by means of screws 23 is removably connected. Threaded openings 24 are provided in flanges 24' connected to sidewalls 17. As best shown in FIG. 2 the sampler apparatus also includes converging wall portions 25 which are in communication and connected to a rectangular chute 26, which is provided as best shown in FIG. 1 with a hopper or collector end 27 positioned within the tubular or conduit member 11 to direct a certain amount of the passing product into the sampler unit.

The collector end 27 may also be designated as the primary cutter which is of a width to collect a representative sample of the sponge iron mix which passes into the conveyor or chute 10.

Figure 3:
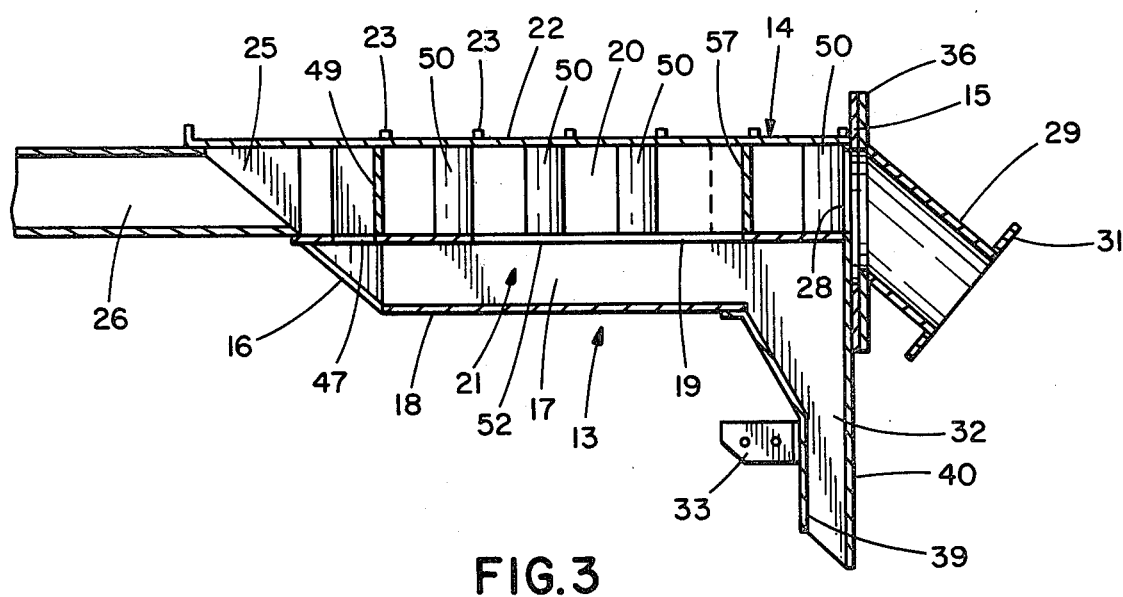
FIG. 3 is a cross-sectional view taken along the line 3—3 of FIG. 2.

As best shown in FIGS. 2 and 3 one end of the chamber 20 is provided with an opening 28, in the end wall 15, the same providing communication between the chamber and a discharge pipe 29. The discharge pipe 29 includes flange 30 which is secured over flange 36 connected to the wall 15 over the opening 28. As shown in FIG. 1 the flange 31 is connected to a flange 41 of a pipe 42 which conveys the sample to a suitable sampling station.

FIGS. 2 and 3 disclose a vertical discharge channel 32 having connected thereto a bracket 33 which in turn connects the sampler in the position shown in FIG. 1 on the tubular member or structure 11. The bracket 33 is suitably connected to the bracket 34 projecting outwardly from the tubular member and secured thereto by means of fasteners 35.

As shown in FIG. 2 the intermediate wall 19 has cutouts as indicated at 37 to provide a pair of triangular openings 38 which are positioned adjacent to the discharge pipe 29 on opposite sides thereof. The wall 15 includes a lower extension wall 40 forming a vertical discharge channel or chute 32 by means of the parallel vertical wall 39. The chute 32, as best shown in FIG. 1, has its end extending through an opening 56 provided in the tubular member 11 so as to return material or product from the chamber 21 into the conveyor housing 11. Material which has entered through the discharge pipe 29 is of course directed by means of the pipe 42 to the product sampling station.

The configuration of the baffles and openings in the intermediate wall are best shown in FIG. 2 and comprise adjacent to the chute 26 a row of wall openings 43 each set of openings being designated by the reference character 44. The openings 44 are all the same size and are relatively square having upstanding front baffles 46 which deflect material coursing into the openings downwardly and inwardly so that the material is segregated from the upper chamber into the lower chamber. In addition to the row of openings 43 larger end openings 47 are of rectangular shape and are positioned in contiguous relation to the diverging walls 25, the said openings 47 also diverting sponge iron pellets downwardly into the lower chamber 21. The larger openings 47 are provided with upwardly extending flanges 48 and 49 which act as baffles or deflectors to assist in diverting the pellets to the lower chamber.

As can be seen from FIG. 2 the intermediate wall 19 is also provided with a plurality of baffles 50 suitably connected to the flat upper surface of the intermediate wall 19. The baffles are of V-shaped configuration consisting of interconnected upright walls and are also in turn in V-shaped row configuration, the two rows emanating from the baffles 50, located immediately to one side of the discharge opening, and then diverging outwardly in the manner indicated. The configuration thus provides for a narrow corridor 51 which permits entrance of the pellets to advance through the discharge pipe 29, providing the samples desired. The disposition of the baffles is such that the pieces are discharged through the large openings 38, 52, and 58. The large opening 52 is provided with a vertically extending upright wall 54 on one side and includes on its other side the V-shaped baffles and deflectors and also includes upright walls 55 and 55' which again effectively block the openings 50 from entrance of certain pellets of sponge iron.

In the present samples the primary cutter in forms of the chute 27 revenues a large quantity of sample representative of the product mix which then enters into the secondary cutter 13. Initially the secondary cutter 13 provides for a quantity of the sample to be released through the openings 44 thus cutting the quantity of sample materially whereupon the reduced sample portion is diverted toward and into the discharge pipe 29. Thus in the present arrangement only a portion of the product is delivered to the sampler unit and from that which is so delivered only a portion is diverted into the sample tube for subsequent sampling. It is believed that the present invention provides for a more efficient sampling of product such as sponge iron.

I claim:

1. For a conveyor adapted to convey a pelletized product, said conveyor having a tubular wall provided with an opening in one side thereof, the improvement of a product sampling apparatus comprising:
 a housing including side walls and end walls,
 a lower wall,
 an intermediate wall,
 a cover wall, with said walls interconnected to provide an upper and lower chamber,
 a first outlet connection communication with said upper chamber adjacent a first end thereof,
 a second outlet connection communicating with said lower chamber,
 an inlet chute connected to said upper chamber adjacent a second opposite end thereof,
 means connecting said sampling apparatus in inclined planar relation to said conveyor side wall whereby said inlet chute communicates with the interior of the conveyor to direct product to said upper chamber,
 baffle means on said intermediate wall in said upper chamber disposed in the path of movement of said product,
 sorting apertures in said intermediate wall communicating with said lower chamber,
 said baffle means and sorting apertures being arranged and constructed to direct and divide a larger quantity of product into smaller representative pelletized samples whereupon they are respectively discharged from said chambers through said first and second outlet connectors,
 said sorting apertures including a first row positioned adjacent to said inlet chute and said row extending transversely with respect thereto,
 said row of apertures including at opposite ends thereof apertures of larger size than the other apertures of said row, the latter being positioned adjacent to the side walls of said apparatus.

2. The apparatus in accordance with claim 1,
 said side walls adjacent to said larger apertures extending diagonally inwardly from said inlet chute.

3. The apparatus in accordance with claim 1,
 said intermediate wall having second baffle means disposed on opposite sides of said first outlet connection to deflect product to and away from said first outlet connection.

4. For a conveyor adapted to convey a pelletized product, said conveyor having a tubular wall provided with an opening in one side thereof, the improvement of a product sampling apparatus comprising:
 a housing including side walls and end walls,
 a lower wall,
 an intermediate wall,
 a cover wall, with said walls interconnected to provide an upper and lower chamber,
 a first outlet connection communication with said upper chamber adjacent a first end thereof,
 a second outlet connection communicating with said lower chamber,
 an inlet chute connected to said upper chamber adjacent a second opposite end thereof,
 means connecting said sampling apparatus in inclined planar relation to said conveyor side wall whereby said inlet chute communicates with the interior of the conveyor to direct product to said upper chamber,
 baffle means on said intermediate wall in said upper chamber disposed in a path of movement of said product, sorting apertures in said intermediate wall communicating with said lower chamber, said baffle means and sorting apertures being arranged and constructed to direct and divide a larger quantity of product into smaller representative pelletized samples whereupon they are respectively discharged from said chambers through said first and second outlet connectors, said sorting apertures including a first row positioned adjacent to said inlet chute and said row extending transversely with respect thereto, said intermediate wall having second baffle means disposed on opposite sides of said first outlet connection to deflect product to and away from said first outlet connection, said intermediate wall having second sorting apertures disposed on opposite sides of said first outlet connection.

5. The apparatus in accordance with claim 4, said intermediate wall having two rows of V-shaped baffle members, each positioned from the other in horizontally spaced relation and extending from said second baffle means in V-shaped configuration.

6. The apparatus in accordance with claim 5, said sorting apertures including a relatively larger aperture having vertically extending deflector walls, said larger aperture being positioned in blocking relation with respect to said first outlet connection.

7. The apparatus in accordance with claim 3, said vertically extending deflector walls being positioned around said larger aperture and with said second baffle means providing a restricted relatively narrow path for product moving toward said first outlet connection.

8. The invention in accordance with claim 4, said second sorting apertures being of triangular shape, substantially large and contiguous with said end wall adjacent to said first end of said upper chamber.

* * * * *